United States Patent
Nyström et al.

[19]

[11] Patent Number: 5,900,111
[45] Date of Patent: May 4, 1999

[54] PROCESS FOR SANITIZING POST-CONSUMER PAPER FIBERS USING HEAT AND HYDROGEN PEROXIDE

[75] Inventors: Tommy Nyström, Lund, Sweden; Hyder Ali, Federal Way, Wash.; Fritz Lembke, Erligheim, Germany

[73] Assignee: Tetra Laval Holdings & Finance S.A., Pully, Switzerland

[21] Appl. No.: 08/967,332

[22] Filed: Oct. 21, 1997

Related U.S. Application Data

[63] Continuation of application No. 08/606,643, Feb. 27, 1996, abandoned.

[51] Int. Cl.$^6$ ................................... D21C 5/02
[52] U.S. Cl. ........................ 162/6; 162/8; 162/161
[58] Field of Search ............... 162/4, 6, 8, 28, 162/161

[56] References Cited

U.S. PATENT DOCUMENTS

| | | | |
|---|---|---|---|
| 2,525,594 | 10/1950 | Fennell | 92/1.5 |
| 3,440,134 | 4/1969 | Murphy | 162/8 |
| 3,514,278 | 5/1970 | Brink | 71/67 |
| 3,766,001 | 10/1973 | Gleason et al. | 162/8 |
| 4,160,693 | 7/1979 | Lindahl et al. | 162/24 |
| 4,207,139 | 6/1980 | Haikkala et al. | 162/23 |
| 4,207,140 | 6/1980 | Lindahl | 162/23 |
| 4,244,778 | 1/1981 | Lindahl et al. | 162/17 |
| 4,253,945 | 3/1981 | Karnis | 209/211 |
| 4,270,976 | 6/1981 | Sandstrom et al. | 162/26 |
| 4,311,553 | 1/1982 | Akerlund et al. | 162/23 |
| 4,377,439 | 3/1983 | Liem | 162/30.1 |
| 4,381,969 | 5/1983 | De Ceuster et al. | 162/5 |
| 4,390,395 | 6/1983 | De Ceuster et al. | 162/5 |
| 4,444,621 | 4/1984 | Lindahl | 162/26 |
| 4,561,933 | 12/1985 | Wood et al. | 162/5 |
| 4,812,206 | 3/1989 | Devic et al. | 162/25 |
| 4,900,399 | 2/1990 | Bengtsson et al. | 162/26 |
| 4,964,444 | 10/1990 | Hanerus et al. | 141/90 |
| 5,008,076 | 4/1991 | Johansson et al. | 422/28 |
| 5,011,664 | 4/1991 | Olanders | 422/292 |
| 5,114,671 | 5/1992 | Olanders | 422/28 |
| 5,143,581 | 9/1992 | Devic | 162/72 |
| 5,147,503 | 9/1992 | Nguyen | 162/7 |
| 5,169,495 | 12/1992 | Lachenal | 162/78 |
| 5,183,644 | 2/1993 | Martensson et al. | 422/304 |
| 5,211,809 | 5/1993 | Naddeo et al. | 162/6 |
| 5,234,544 | 8/1993 | Naddeo | 162/5 |
| 5,258,162 | 11/1993 | Andersson et al. | 422/228 |
| 5,296,100 | 3/1994 | Devic | 162/78 |
| 5,298,118 | 3/1994 | Devic | 162/26 |
| 5,326,542 | 7/1994 | Sizer et al. | 422/291 |
| 5,350,568 | 9/1994 | Tuckner et al. | 422/300 |
| 5,356,592 | 10/1994 | Balla et al. | 422/28 |
| 5,368,828 | 11/1994 | Carlson | 422/300 |
| 5,390,860 | 2/1995 | Ali et al. | 241/20 |
| 5,665,205 | 9/1997 | Srivatsa et al. | 162/181.4 |

FOREIGN PATENT DOCUMENTS

| | | |
|---|---|---|
| 0566284 | 10/1993 | European Pat. Off. . |
| WO95/00439 | 1/1995 | WIPO . |

OTHER PUBLICATIONS

Sales Brochure, James River Corporation, Aug. 1994.
"Microbiological Contamination of Recycled Papers and Boards—Optimisation of Decontamination Processes", Escabasse et al., Oct. 5–6, 1995.

*Primary Examiner*—Stanley S. Silverman
*Assistant Examiner*—Dean T. Nguyen
*Attorney, Agent, or Firm*—Burns, Doane, Swecker & Mathis, L.L.P.

[57] ABSTRACT

The invention relates to a process for sanitizing post-consumer wastepaper fibers for liquid packages and containers, a paper product for food packaging and a liquid food container. The process comprises providing paper fibers from a wastepaper recycle process, adding water to the paper fibers to achieve a slurry, de-watering the slurry to obtain a paper fiber stream and passing the fiber stream through a mixing device while heating the fiber stream and supplying hydrogen peroxide in the mixing device.

25 Claims, 3 Drawing Sheets

PROCESS FOR SANITIZING POST-CONSUMER PAPER FIBERS USING HEAT AND HYDROGEN PEROXIDE

This application is a continuation of application Ser. No. 08/606,643, filed Feb. 27, 1996 now abandoned.

FIELD OF THE INVENTION

This invention relates to the recovery and use of paper fibers from scrap paper, and more particularly to a process for sanitizing paper fibers for use in food-contact materials such as packaging, liquid food containers, and the like.

BACKGROUND OF THE INVENTION

Various processes for recovering paper fibers from scrap paper such as paperboard food cartons and packages, office waste paper, magazines and newspapers have been proposed. Typically, these recycle processes involve treating the waste paper in a hydrapulping machine wherein the fibers are separated by the agitation of the water, and the use of caustic soda or similar reagents break down the integrity of the waste paper. This results in a stream of separated paper fibers which may be passed through various screening devices to remove contaminants, and the resulting slurry containing the paper fibers may pass through a de-inking process. After appropriate treatment, which may include bleaching, the slurry of paper fibers passes through a de-watering stage, so that the recovered paper fibers are collected in an essentially dry state and may be packed in bales for subsequent use in making paper. An example of a recycle process that would be suitable for obtaining dry paper fibers is disclosed in U.S. Pat. No. 5,390,860, "Method and Apparatus for Separating Paper Fiber and Plastics from Mixed Waste Materials", which is incorporated herein by reference.

If recovered paper fibers are to be used for making packages or containers for food products, government regulations require that they meet the same standards as for virgin paper fibers, e.g., the recommendation by the International Dairy Federation (IDF) of a maximum bacterial load of 250 colony-forming units per gram ("cfu/g").

In a typical paper plant, virgin pulp is digested and bleached in a slurry that is supplied directly to the paper-making machine. Recycled paper fibers are often processed in local recycle plants, dried, stored in bales, and subsequently transported to paper-making plants for further processing into cartons and containers. While the bales of fibers are being stored, microorganisms that are present may multiply and cause contamination of the final paper product. It has been proposed to sterilize recycled fibers by heating the fibers to a pasteurizing temperature. However, this sterilization process requires steam-heating equipment and vessels, and thus can be very expensive. Addition of bactericides to a dilute pulp slurry has also been proposed to control bacterial load in food packaging, but also requires substantial input of energy and chemicals to achieve the desired results. Moreover, use of bactericides may leave undesirable residues in the pulp. The efficiency and economy of the recycle process is important because of the substantial costs incurred in obtaining the recycled fibers. For recycling to succeed as an economically feasible process, these costs must be as low as possible while achieving the desired sanitary standards.

Among the microorganisms most difficult to kill are spore-forming bacteria. Spore-formers can survive the drying temperatures which are normally employed in a paper-making machine. If these spore-formers are present in the paper fibers that are supplied to the paper-making machine, the resulting paper and paperboard are likely to have substantially more than the 250 limit of colony-forming units per gram ("cfu/g").

OBJECTS AND SUMMARY OF THE PREFERRED EMBODIMENTS

The present invention provides a process for treating recycled paper fibers to make paper or paperboard containing bacterial spore-former amounts of 250 cfu/g or less.

This invention also provides a process for sanitizing recycled paper fibers in an effective and efficient manner.

In accordance with this invention, pulp/paper fibers are obtained from a paper recycle plant, paper mill or other source. If the fibers are obtained in an essentially dry condition, water is added to the dry fiber mass to achieve a consistency of about 0.5–5%, preferably 2–4%, fiber by weight on a dry content basis. The mixture is later de-watered to increase the consistency to 10–40%, and preferably about 30–35%, by weight on a dry content basis. This product is supplied to a mixing device which processes a continuous stream of the moistened fibers. The mixing device is supplied with steam, preferably between about 160° C. and about 170° C., and a dilute hydrogen peroxide solution. If needed, sufficient sodium hydroxide may be added to adjust the pH of the fiber mixture to about pH 6–8, preferably about pH 7. Thus the fiber stream is heated in the mixing device ultimately to over 80° C., preferably to at least 90° C., and treated with hydrogen peroxide. The final $H_2O_2$ concentration in the fiber mixture is preferably about 0.5–5% by volume, based on the total volume of the mixture. The contents of the mixing device may also be pressurized during the sanitizing process. The combination of hydrogen peroxide and heat treatment produces a more efficient and effective spore-killing process than heat alone. The residence time for the fiber stream as it passes through the mixing device is about 0.5–5 minutes. Additional water may be supplied to adjust the consistency and temperature of the sanitized fiber stream as required for making pulp or paperboard. The adjusted fiber stream may then be conducted to a papermaking machine for making paper or paperboard for use in food-contact materials, such as food packaging, liquid food containers, and paper towels.

BRIEF DESCRIPTION OF THE DRAWINGS

A preferred embodiment of the invention is illustrated in the accompanying drawings in which.

DETAILED DESCRIPTION OF THE PREFERRED EMBODIMENTS

Various conventional processes are available for treating waste paper, newspaper, magazines and office paper to recover paper fibers. Typically, the paper fibers may be stored and transported in bales in an essentially dry condition prior to their treatment by the sanitizing process of this invention.

Figure 1:
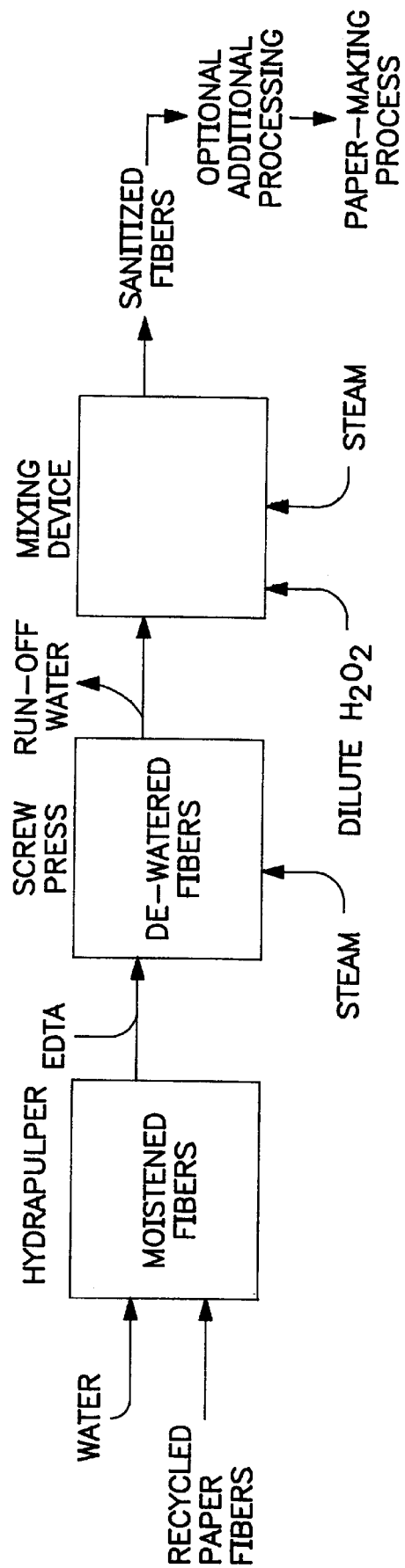
FIG. 1 is a schematic representation of a non-pressurized embodiment of the sanitizing process of the invention.

As shown in FIG. 1, the dry paper fibers are introduced into a hydrapulper with sufficient water to form a slurry having a consistency of about 0.5–5%, preferably 2–4% fiber by weight. This step usually occurs at ambient temperature. The slurry in the hydrapulper normally will be slightly alkaline due to the presence of alkali used in the paper fiber recovery process. Optionally, the pulp slurry may undergo several mechanical or chemical treatments to remove various contaminants, preferably prior to de-watering of the slurry. For example, a chelating agent, such as ethylenediaminetetraacetic acid (EDTA), may be added to the pulp slurry in an amount effective to complex any metal ion residues in the pulp.

The water content in the slurry is reduced by a screw press, to obtain a continuous stream of moistened fibers having the consistency of soft clay, with a fiber content of about 10–40%, preferably about 30–35%. This paper fiber stream is supplied to a mixing device which processes the fiber stream. The mixing device may be a kneader having parallel feed screws for thorough mixing of the pulp fiber stream. The mixing device may be, for example, a horizontal mixer such as a "LAMORT" triturator.

The mixing device, containing the fiber stream, is then supplied with steam to heat the fiber stream; a dilute hydrogen peroxide solution; and, optionally, sufficient sodium hydroxide to adjust the pH of the pulp paper mixture to pH 7 or a more alkaline pH.

The temperature of the added steam is preferably such as to bring the fiber stream to a temperature of over 80° C., preferably at least 90° C. In a non-pressurized embodiment of the process, the fiber/$H_2O_2$ mixture is brought first to a temperature of about 70° C., to open up the spores and thus make them less resistant to heat, then to a temperature of over 80° C., preferably at least 90° C., e.g., 82–99° C., to kill the spores.

Figure 2:
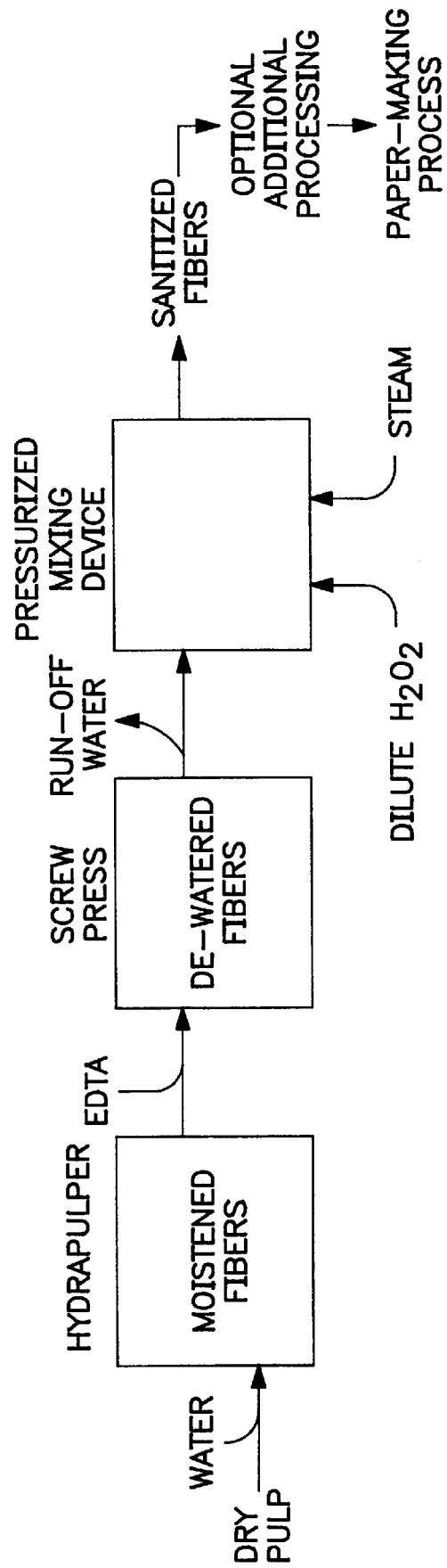
FIG. 2 is a schematic representation of a pressurized embodiment of the sanitizing process.

Alternatively, especially good results can be achieved efficiently and cost-effectively in a pressurized system, shown in FIG. 2, by bringing the fiber stream to a temperature of over 90° C., preferably about 110–115° C., under pressure, at various combinations of hydrogen peroxide concentrations and treatment times. The added steam is preferably at a temperature of about 160–170° C. and pressurized, e.g., to about 8 bar.

The dilute hydrogen peroxide solution may be at a concentration of, for example, about 30–70%, preferably 30–50%, and most preferably 30–35 wt %. Preferably, the hydrogen peroxide solution is added in an amount sufficient to achieve a concentration of about 0.1–5% by volume, which corresponds to 0.3 kg peroxide/ton to 1.7 kg peroxide/ton (assuming a pulp consistency of 33% when adding the peroxide). This concentration is preferably 2–4%, and most preferably about 3% by volume in the moistened paper fiber stream (calculated on the total volume). As in the non-pressurized system, pH of the pulp paper mixture can be adjusted to a pH of 7 or more. Moreover, hydrogen peroxide is preferably added during the process when the recycled pulp mixture has a relatively high dry-matter content, e.g., about 30–35% fibers.

The residence time for the fiber stream as it passes through the mixing device (e.g., a kneader) is about 0.5–5 minutes, preferably 2–4 minutes, most advantageously about 3 minutes. For example, two parallel feed screws are typically employed to advance the fiber stream through the kneader at the desired speed.

The treated fiber stream that passes out of the mixing device has a higher moisture content due to the introduction of the steam. Water may be removed or additional water may be supplied, as desired, to adjust the consistency and temperature of the treated fiber stream as required for making paper or paperboard. Any added water should be substantially free of pathogenic microorganisms to avoid recontamination. The final sanitized product may be brown or white. The sanitized fiber stream can then be treated further, and/or be used alone or mixed with virgin pulp to make paper. For instance, the fiber stream is conducted, preferably directly and in substantially sterile conditions, to a papermaking machine for making paper or paperboard for consumer use, e.g., liquid food packaging and containers.

An advantageous embodiment of the sanitizing process of the invention treats the pulp at over about 90° C., for about 0.5–5 minutes, with low hydrogen peroxide concentrations of about 0.1–5%, preferably 0.5–4% by volume, based on the total volume of the fiber stream in the mixing device. Especially advantageous is treatment at temperatures of about 110–115° C. with about 2–4%, especially 3%, $H_2O_2$ by volume, for about 2–4, especially 3 minutes, which gives an acceptable spore count in the treated pulp. These temperature and $H_2O_2$ concentration ranges are particularly advantageous in giving an acceptable microbial load in recycled paper fiber of $\leq 250$ cfu/g while maintaining good cost-effectiveness, efficiency, and minimal environmental impact. Lower temperatures could be used along with higher $H_2O_2$ concentrations to achieve sufficient spore-killing. However, at a certain point, higher $H_2O_2$ would increase sanitizing costs and environmental effects, particularly if additional chemicals are required to neutralize residual $H_2O_2$.

In an advantageous embodiment, recycled pulp treated at temperatures higher than 95° C. along with at least 3% hydrogen peroxide, based on total volume of the fiber stream in the mixing device, achieves sufficient spore-killing effect with an approximate log 3 to log 4 reduction in bacterial load.

The sanitizing process of the present invention thus provides sanitized, recycled pulp/paper fibers having not only low bacterial load, but also having very few or no chemical residues such as hydrogen peroxide. This advantage results from chemical and/or heat effected degradation of the hydrogen peroxide during the sanitizing process. Hence, the process of the invention also meets the recommendation of the German government, Budesinstitut für Gesundheitlichen Verbraucherschutz und Veterinärmedizin D-Berlin (formerly Bundesgesundheitsamt, BGA), BGA 36 VII B, which requires the final paper/paperboard product to contain no or insignificant amounts of chemical residues.

EXAMPLE 1

Evaluation of Bacterial Spore Reduction in Sanitized Pulp

The following tests were performed to assess the results of the sanitizing process of the invention. Reduction of bacterial load in pulp recycled from old liquid packages ("OLP") was determined for various combinations of heat and hydrogen peroxide concentrations, the goal being to achieve a bacterial load of $\leq 250$ cfu/g.

1. Test Parameters

Tests focused on the reduction of aerobic and anaerobic bacterial spore-formers (e.g., Bacillus, Clostridia, ascospore-forming moulds). Aerobic spore-formers are among the most resistant flora in pulp and hence, are among the most relevant microorganisms for determining compliance with the maximum bacterial load of 250 cfu/g in pulp used to make paper or paperboard products. In particular, not all aerobic spore-formers need be included in total colony counts, because spore proliferation requires certain activation temperatures. Those temperatures are below 80° C. and hence, generally below the spore-killing temperatures employed in the process of the invention.

The presence of vegetative bacterial cells in the treated pulp also does not matter as they are efficiently killed during subsequent paper manufacturing processes.

Anaerobic spore-formers, while relevant in terms of public health requirements, are generally more heat-labile than aerobic spore-formers. Therefore, temperatures which aid in reducing aerobic spore-formers in the process of the invention also reduce anaerobic spore-formers and other bacteria.

Samples were taken of recycled pulp treated according to the process of the invention, during trials at a pilot recycling plant. Only tap water of good microbial quality (e.g., $\leq 1$ spore/ml) was used to re-dilute the treated pulp samples, to avoid contamination of the sanitized pulp prior to evaluation of the effectiveness of the sanitizing process. All samples were analyzed for aerobic spore counts directly after sampling to avoid counting any later spore reduction caused by any sterilant residue left in the pulp.

2. Sample Preparation

Directly after sampling, 10 grams of a pulp sample were diluted with 90 ml of 2% thiosulfate solution and homogenized in a sterile "STOMACHER" bag for 5 minutes. Ten ml of the resulting supernatant were heated at 80° C. for about 10–12 minutes in a water bath prior to determining spore counts. Heating the prepared samples to 80° C. eliminates from the count, certain aerobic spore-formers which do not proliferate unless they are at a certain activation temperature, i.e., below 80° C.

3. CFU Evaluation

The number of colony-forming units per gram of dry matter content of the pulp sample (cfu/g) is calculated as follows:

cfu/g dry matter = (cfu/ml sample) ×
(dilution factor of sample) × (100/% dry matter content of pulp)

3.1 Aerobic Spore-Former Colony Count

Aerobic spore-former (e.g., Bacillus) colony counts were determined by standard plate counts of pulp samples directly after sample preparation, according to the DIN 54379 method for determining total counts in paper and board. Ten grams of pulp sample were diluted in 90 ml of Ringers solution and homogenized in a sterile "STOMACHER" bag for about 5 minutes. The colony count was determined by using ten-fold dilutions of the homogenized pulp samples. Sample dilutions were incubated on Agar plates at about 35±2° C., and evaluated for aerobic spore-former counts after 24 hours and again after 48 hours.

3.2 Total Count

Pulp samples were also analyzed for total counts at Tetra Pak Research Laboratory, Stuttgart, after storage at 0° C. for approximately 4–6 days. Strictly speaking, total counts are of aerobic microorganisms, as anaerobes are determined under different conditions (see below). Ten grams of pulp were diluted with 90 ml of 2% thiosulphate solution, homogenized in a sterile "STOMACHER" bag at ambient temperature for 5 minutes, poured onto Plate Count Agar (PC-Agar) plates, and incubated at 30° C. for 3 days to determine total count.

3.3 Anaerobic Sulphite-Reducing Spore-Former Counts

Anaerobic spore-former counts were determined by treating samples substantially as described above for determining total counts, except that after homogenization in a "STOMACHER", samples were heated at 80° C. for 10 minutes and sample dilutions were incubated on TSC-Agar (Tryptose-sulphite-cycloserine agar or TSC) plates in anaerobic jars at 37° C. for 3–5 days.

3.4 Enterobacteriaceae Counts

Samples of pulp were treated as for determining total aerobic counts. Samples were then incubated on Violet Red Bile Dye Agar (VRBD-Agar) plates for 24 hours at 37° C. to determine Enterobacteriaceae counts. Enterobacteriaceae are Gram-negative, aerobic spore-formers which can be facultative anaerobes and include E. coli.

4. Measurement of pH

The pH of each pulp sample was determined by electrometric measurement.

5. Statistics

Experimental design and statistical analysis of test results was performed with the computer software, STATGRAPHICS (Version 7, Manugistics Inc., 1993).

6. Results and Discussion of Example 1

Pulp was treated with hydrogen peroxide at different temperatures (75° C. or 115° C.), different times (2 or 4 minutes) and different concentrations (0.5% or 1.5% $H_2O_2$ by weight based on dry pulp weight, which corresponds to 0.15% and 0.45%, respectively, by volume of the treated fiber mixture). Counts of aerobic spores were then determined, and presented in Table 1, as Total cfu/g, Log cfu/g, and Log Reduction (the difference in Log cfu/g values before and after treatment). Table 1 shows that hydroxide peroxide treatment at 75° C. gives a spore reduction effect of about log 2, but at 115° C., gives an even greater reduction effect of about log 5. The final spore load of the 115° C. treated samples is well below the allowable limit of 250 cfu/g for paper products.

The aerobic spore reduction effects of the process of the invention cannot result from the heating step alone, because they are significantly greater than known decimal reduction values ("D-values") for aerobic spore-formers treated by heat alone. These "D-values" define the time necessary for a decimal reduction (1 log) in bacteria under fixed heat/ chemical treatment condition in minutes. For instance, Wallhäußer (1995, Springer Verlag Stuttgart New York), in *Praxis der Sterilisation Desinfektion Konservierung* (1984, Springer Vertag), describes a $D_{115}$"-value of 2.2 min at 115° C. for a mesophilic *Bacillus subtils*. Baumgart, in *Mikrobiologische Untersuchung von Lebensmittein* (1994), describes $D_{121}$"-values of 2.35 min. at 121° C. and for *Bacillus licheniformis* a $D_{100}$"-value of 2.0 to 4.5 min. at 100° C. Therefore, the D-values of around 4 or more log achieved in Example 1 by the process according to the invention (see, Reduction values in Tables 1–4) cannot be achieved by heat alone without a sterilant. This conclusion is further supported by the reduction effect obtained by hydrogen peroxide treatment at only 75° C. by the process according to the invention using hydrogen peroxide. Generally, without using $H_2O_2$ at that temperature, spore-formers are not inactivated or killed but, in fact, are activated to proliferate.

TABLE 1

Aerobic spore counts in pulp before and after treatment with hydrogen peroxide at different temperatures and concentrations

| Sample Number | Temperature (° C.) | $H_2O_2$ Conc. (% dry wt.) | Time (min.) | pH | Consistency (% pulp) | Total cfu/g | Log cfu/g | Log Reduction |
|---|---|---|---|---|---|---|---|---|
| *Before Treatment* | | | | | | | | |
| 1, 2 | — | — | — | 7.08 | 35.9 | 2.23E + 05 (223,000) | 5.35 | — |
| 3, 4 | — | — | — | 7.51 | 21.1 | 5.45E + 05 (545,000) | 5.74 | — |
| 5, 6 | — | — | — | 7.34 | 38.5 | 3.51E + 05 (351,000) | 5.54 | — |
| 7, 8 | — | — | — | 7.51 | 35.7 | 3.92E + 05 (392,000) | 5.59 | — |
| *After Treatment* | | | | | | | | |
| 1 | 75 | 0.5 | 2 | 8.01 | 24.4 | 9.02E + 03 (9,020) | 3.96 | 1.4 |
| 2 | 75 | 0.5 | 4 | 7.53 | 20.2 | 2.11E + 03 (2,110) | 3.32 | 2.0 |
| 3 | 75 | 1.5 | 4 | 7.74 | 21.9 | 7.51E + 03 (7,510) | 3.88 | 1.9 |
| 4 | 75 | 1.5 | 2 | 7.61 | 25.7 | 3.74E + 03 (3,740) | 3.57 | 2.2 |
| 5 | 115 | 0.5 | 2 | 7.44 | 37.1 | 5.39E + 00 (5.39) | 0.73 | 4.8 |
| 6 | 115 | 0.5 | 4 | 7.21 | 30.1 | 8.31E + 01 (83.1) | −0.08 | 5.6 |
| 7 | 115 | 1.5 | 4 | 7.17 | 34.0 | 3.43E + 00 (3.43) | 0.54 | 5.1 |
| 8 | 115 | 1.5 | 2 | 6.47 | 26.0 | 3.85E + 00 (3.85) | 0.59 | 5.0 |

Pulp samples were stored for approximately 1 week at 0° C. prior to determining the total count, sulphite-reducing anaerobic spore count, and Enterobacteriaceae count.

Table 2 summarizes total aerobic counts in pulp stored at 0° C. for about 1 week, before and after treatment with hydrogen peroxide at concentrations of 0.5% or 1.5% by weight based on dry pulp weight, for 2 or 4 minutes and at 75° C. or 115° C. After 1 week of storage, the total aerobic count in pulp treated at 115° C. was still very low, being around 30 cfu/g. In contrast, stored samples of pulp treated at 75° C. displayed relatively high total aerobic counts of up to about log 8 cfu per gram of dry matter (log cfu/g).

Table 3 summarizes anaerobic spore-former counts in treated pulp after one week of storage at 0° C. Treatment of pulp with hydrogen peroxide, particularly at the concentrations, temperatures and lengths of time shown, also resulted in low levels of sulphite-reducing anaerobic spore-formers.

Table 4 summarizes the Enterobacteriaceae counts in treated pulp after one week of storage at 0° C. Comparison of the total cfu/g and log cfu/g values show that hydrogen peroxide treatment of pulp, particularly at the temperatures, concentrations and treatment times shown, also largely resulted in low Enterobacteriaceae counts after 1 week of storage at 0° C.

TABLE 2

Total aerobic count in treated pulp after 1 week storage at 0° C.

| Sample Number | Temperature (° C.) | $H_2O_2$ Conc. (% by wt. of dry pulp) | Time (min.) | pH | Consistency (% pulp) | Total cfu/g | Log cfu/g | Log Reduction |
|---|---|---|---|---|---|---|---|---|
| *Before Treatment* | | | | | | | | |
| 1, 2 | — | — | — | 7.08 | 35.9 | 2.40E + 07 (24,000,000) | 7.38 | — |
| 3, 4 | — | — | — | 7.51 | 21.1 | 1.45E + 08 (145,000,000) | 8.16 | — |
| 5, 6 | — | — | — | 7.34 | 38.5 | 8.05E + 07 (80,500,000) | 7.91 | — |
| 7, 8 | — | — | — | 7.51 | 35.7 | 6.44E + 07 (64,400,000) | 7.81 | — |
| *After Treatment* | | | | | | | | |
| 1 | 75 | 0.5 | 2 | 8.01 | 24.4 | 2.64E + 08 (2,640,000) | 8.42 | — |
| 2 | 75 | 0.5 | 4 | 7.53 | 20.2 | 7.92E + 03 (7,920) | 3.90 | 3.5 |

TABLE 2-continued

Total aerobic count in treated pulp after 1 week storage at 0° C.

| Sample Number | Temperature (° C.) | H₂O₂ Conc. (% by wt. of dry pulp) | Time (min.) | pH | Consistency (% pulp) | Total cfu/g | Log cfu/g | Log Reduction |
|---|---|---|---|---|---|---|---|---|
| 3 | 75 | 1.5 | 4 | 7.74 | 21.9 | 5.25E + 07 (52,500,000) | 7.72 | 0.4 |
| 4 | 75 | 1.5 | 2 | 7.61 | 25.7 | 6.03E + 04 (60,300) | 4.78 | 3.4 |
| 5 | 115 | 0.5 | 2 | 7.44 | 37.1 | 2.70E + 01 (27.0) | >1.43 | >6.5 |
| 6 | 115 | 0.5 | 4 | 7.21 | 30.1 | 3.32E + 01 (33.2) | >1.52 | >6.4 |
| 7 | 115 | 1.5 | 4 | 7.17 | 34.0 | 2.94E + 01 (29.4) | >1.47 | >6.3 |
| 8 | 115 | 1.5 | 2 | 6.47 | 26.0 | 3.85E + 01 (38.5) | >1.59 | >6.2 |

TABLE 3

Anaerobic spore-former count in treated pulp after 1 week storage at 0° C.

| Sample Number | Temperature (° C.) | H₂O₂ Conc. (% by wt. of dry pulp) | Time (min.) | pH | Consistency (% fiber) | Total cfu/g | Log cfu/g | Log Reduction |
|---|---|---|---|---|---|---|---|---|
| Before Treatment ||||||||| 
| 1, 2 | — | — | — | 7.08 | 35.9 | — | — | — |
| 3, 4 | — | — | — | 7.51 | 21.1 | 2.56E + 05 (258,000) | 5.41 | — |
| 5, 6 | — | — | — | 7.34 | 38.5 | 1.88E + 04 (18,800) | 4.27 | — |
| 7, 8 | — | — | — | 7.51 | 35.7 | 1.93E + 03 (1,930) | 3.29 | — |
| After Treatment ||||||||| 
| 1 | 75 | 0.5 | 2 | 8.01 | 24.4 | 4.10E + 00 (4.10) | 0.61 | 4.8 |
| 2 | 75 | 0.5 | 4 | 7.53 | 20.2 | 4.95E + 00 (4.95) | 0.69 | 4.7 |
| 3 | 75 | 1.5 | 4 | 7.74 | 21.9 | 1.30E + 03 (1,300) | 3.11 | 2.3 |
| 4 | 75 | 1.5 | 2 | 7.61 | 25.7 | 4.09E + 01 (40.9) | 1.61 | 3.8 |
| 5 | 115 | 0.5 | 2 | 7.44 | 37.1 | 2.70E + 00 (2.70) | 0.43 | 3.8 |
| 6 | 115 | 0.5 | 4 | 7.21 | 30.1 | — | — | — |
| 7 | 115 | 1.5 | 4 | 7.17 | 34.0 | 2.94E + 00 (2.94) | 0.47 | 2.8 |
| 8 | 115 | 1.5 | 2 | 6.47 | 26.0 | 3.85E + 00 (3.85) | 0.59 | 2.7 |

TABLE 4

Enterobacteriaceae count in treated pulp after 1 week storage at 0° C.

| Sample Number | Temperature (° C.) | H₂O₂ Conc. (% by wt. of dry pulp) | Time (min.) | pH | Consistency (% pulp) | Total cfu/g | Log cfu/g | Log Reduction |
|---|---|---|---|---|---|---|---|---|
| Before Treatment ||||||||| 
| 1, 2 | — | — | — | 7.08 | 35.9 | 1.24E + 05 (124,000) | 5.09 | — |
| 3, 4 | — | — | — | 7.51 | 21.1 | 1.56 + 05 (156,000) | 5.19 | — |
| 5, 6 | — | — | — | 7.34 | 38.5 | 2.36E + 04 (23,600) | 4.37 | — |
| 7, 8 | — | — | — | 7.51 | 35.7 | 5.04E + 05 (504,000) | 5.70 | — |

TABLE 4-continued

Enterobacteriaceae count in treated pulp after 1 week storage at 0° C.

| Sample Number | Temperature (° C.) | $H_2O_2$ Conc. (% by wt. of dry pulp) | Time (min.) | pH | Consistency (% pulp) | Total cfu/g | Log cfu/g | Log Reduction |
|---|---|---|---|---|---|---|---|---|
| | | | | After Treatment | | | | |
| 1 | 75 | 0.5 | 2 | 8.01 | 24.4 | 4.10E + 06 (4,100,000) | 6.61 | — |
| 2 | 75 | 0.5 | 4 | 7.53 | 20.2 | 4.95E + 00 (4.95) | 0.69 | 4.4 |
| 3 | 75 | 1.5 | 4 | 7.74 | 21.9 | 4.57E + 0 (4.57) | 0.66 | 4.5 |
| 4 | 75 | 1.5 | 2 | 7.61 | 25.7 | 3.89E + 00 (3.89) | 0.59 | 4.6 |
| 5 | 115 | 0.5 | 2 | 7.44 | 37.1 | 2.70E + 00 (2.70) | >0.43 | >3.9 |
| 6 | 115 | 0.5 | 4 | 7.21 | 30.1 | 3.32E + 00 (3.32) | >0.52 | >3.9 |
| 7 | 115 | 1.5 | 4 | 7.17 | 34.0 | 2.94E + 00 (2.94) | >0.47 | >5.2 |
| 8 | 115 | 1.5 | 2 | 6.47 | 26.0 | 3.85E + 00 (3.85) | >0.59 | >5.1 |

The results described in Tables 1–4 demonstrate that hydrogen peroxide treatment of pulp at 115° C. at various treatment times and low concentrations of hydrogen peroxide provides an especially good reduction in the relevant bacterial groups. That is, the most resistant flora, aerobic spores, can be effectively reduced in pulp at a rate of about log 4 to about log 5 by heating the pulp at temperatures of about 115° C. combined with treatment with low hydrogen peroxide concentrations of, e.g., 0.5% and 1.5% by weight based on dry pulp weight (e.g., 0.5 kg and 1.5 kg $H_2O_2$ per metric ton, corresponding to 0.15% and 0.45% $H_2O_2$ by volume, respectively.

Even at 75° C., spore reduction of about log 2 can be achieved by treatment with heat and hydrogen peroxide concentrations of 0.5% and 1.5% by weight (see Table 1).

EXAMPLE 2

Evaluation of Bacterial Spore Reduction in Sanitized Pulp

Additional bacterial load evaluations were performed on sanitized pulp from recycled old liquid packages (OLP), during test runs at a second recycling plant.

1. Test Parameters

The following example demonstrates similarly effective spore reduction at lower temperatures of about 82–99° C., preferably at least 90° C., at a $H_2O_2$ concentration of about 1.5% by volume (based on total volume of the paper fiber mixture), which is equal to about 0.5% by weight peroxide (5 kg peroxide/metric ton fiber mixture).

Bacterial load determinations were performed by an independent laboratory, Silliker Laboratories, Stone Mountain, Ga., USA. The tests included total counts in the final paperboard; aerobic spore counts (as the most resistant microorganisms and the only relevant group in the total count); sulphite-reducing anaerobic spore-formers (e.g., Clostridia); Enterobacteriaceae; and Coagulase-positive Staphylococci. These organisms were studied as being of particular interest for public health concerns.

In this example, the sanitizing process of the invention and comparative treatments were performed in three modules. In module 1, recycled pulp/paper fibers were introduced from a dump chest into a screw press (at ambient temperature) for processing into a pulp slurry. In module 2 the pulp slurry was introduced into a hot kneader to which steam was added. The pulp was heated to about 62–78° C. The heated slurry was then stored at this temperature overnight. In module 3, the pulp slurry was treated in a kneader to which steam was added, and 0.5 wt % $H_2O_2$ (5 kg peroxide/metric ton pulp) was added to the pulp slurry. Treatment temperature was about 82–99° C.

1.1 Sampling Procedure

Samples were taken at different points during the sanitizing process of the invention (see Chart 1 below), placed in sterile "STOMACHER" bags and stored for the duration of the entire sampling procedure in a refrigerator at or below 4° C. Samples were then transported cold (i.e., at ≦4° C.) at least once per day to Silliker Laboratories. All samples which were treated with hydrogen peroxide prior to kneading were diluted at the recycling plant with a 2% sodium thiosulfate solution in order to render the hydrogen peroxide inactive. Directly after sampling, 20 grams of pulp were diluted with 180 ml of 2% sodium thiosulfate.

Tests for the relevant microorganisms, as described below, were only performed on pulp samples taken at the end of module 3 (i.e., 1.5% $H_2O_2$ treatment at 82–99° C.).

1.2 Sampling plan

Samples were taken as follows:

CHART 1

| # | Test Point | Source and Treatment of Samples | Sample Code |
|---|---|---|---|
| 1 | module 1 | 9 samples out of dump chest | BH 1–BH 9 |
| 2 | module 1 end | 10 samples after cold kneader | SP 1–SP 3/8 |
| 3 | module 1 end/2 | 2 samples after hot kneader (first batch using 62–78° C.) | AH 1–AH 2 |
| 4 | module 2 end | 9 samples after hot kneader (after 62–78° C. overnight storage) | AH 3–AH 11 |
| 5 | module 3 end | 8 samples after kneader (1.5% $H_2O_2$, 82–99° C.), with STS | AHP 1–AHP 8 |

-continued

CHART 1

| # | Test Point | Source and Treatment of Samples | Sample Code |
|---|---|---|---|
| 6 | module 3 end/2 | 4 samples after kneader (1.5% $H_2O_2$, 82–99° C.), without STS, determination after 7 days R.T. | AHPS 0– AHPS 9 | legend:
STS - sodium thiosulfate added to samples to render $H_2O_2$ inactive.
R.T. - refrigeration time.

1.3 Sample Preparation

Ten grams of each pulp sample were diluted with 90 ml of a buffered solution and homogenized in a sterile "STOMACHER" for 5 minutes. All samples of pulp treated with hydrogen peroxide (taken at the end of module 3 and the end of module 4) were diluted and homogenized with 2% sodium thiosulfate solution directly after sampling as described under 1.1. Samples were directly taken from these 1:10 dilution for total counts and for pathogenic microorganisms (except for Clostridia).

2. Microbiological Evaluations

Colony-forming units per gram of dry pulp were determined substantially as in Example 1. For the determination of aerobic and anaerobic spores the samples were heated, after dilution and homogenization, for about 10–12 minutes at about 80° C.

2.1 Total Count

Total counts were determined on Plate Count Agar (PC-Agar) after incubation at 30° C. for 3 days. Total count is determined by pouring the diluted samples onto and incubating the plates at 30° C. for 3 days.

2.2 Aerobic Mesophilic Spore Count

The heat-treated and homogenized samples were diluted and plated on PC-Agar to detect aerobic spores, preferably using the surface technique. For 1 ml dilutions pre-dried Agar plates should be used if possible. Plates are incubated at 35±2° C. and aerobic spore counts evaluated after 24 and 72 hours.

2.3 Sulphite-Reducing Anaerobic Spore-Former Count

TSC-Agar is used to test for anaerobic spores in samples first heat-treated at about 80° C. for about 10 min. The plates are then incubated in an anaerobic jar for 3–5 days at 37° C.

2.4 Enterobacteriaceae Count

Enterobacteriaceae counts were determined as described for total count, but on VRBD-Agar incubated for 24 hours at 37° C.

2.5 Coagulase-Positive Staphylococci Count

This determination was made using the Baird-Parker Agar (MERCK) method and confirmed by the Staphyslide-Test (slide test for the identification of *S. aureus*, bio-Merieux, Germany).

2.6 Moulds and Yeast Counts

Evaluations of these microorganisms were done by SILIKER Laboratories using plate count after a 1 week incubation of plates at room temperature.

3. Consistency

The consistency (dry matter content) of the pulp samples was determined on site at the recycling plant.

4. Results

Figure 3:
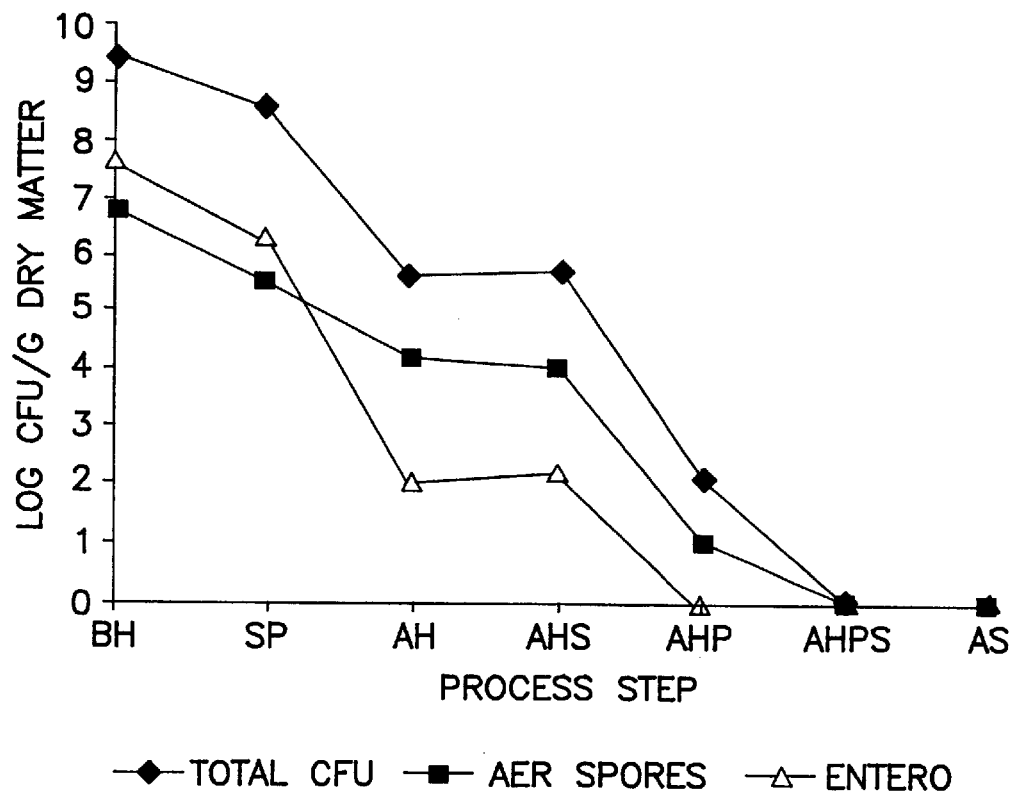
FIG. 3 is a graph of bioburden reduction by the sanitizing process in pulp from old liquid packages (OLP) of Example 1.
Figure 4:
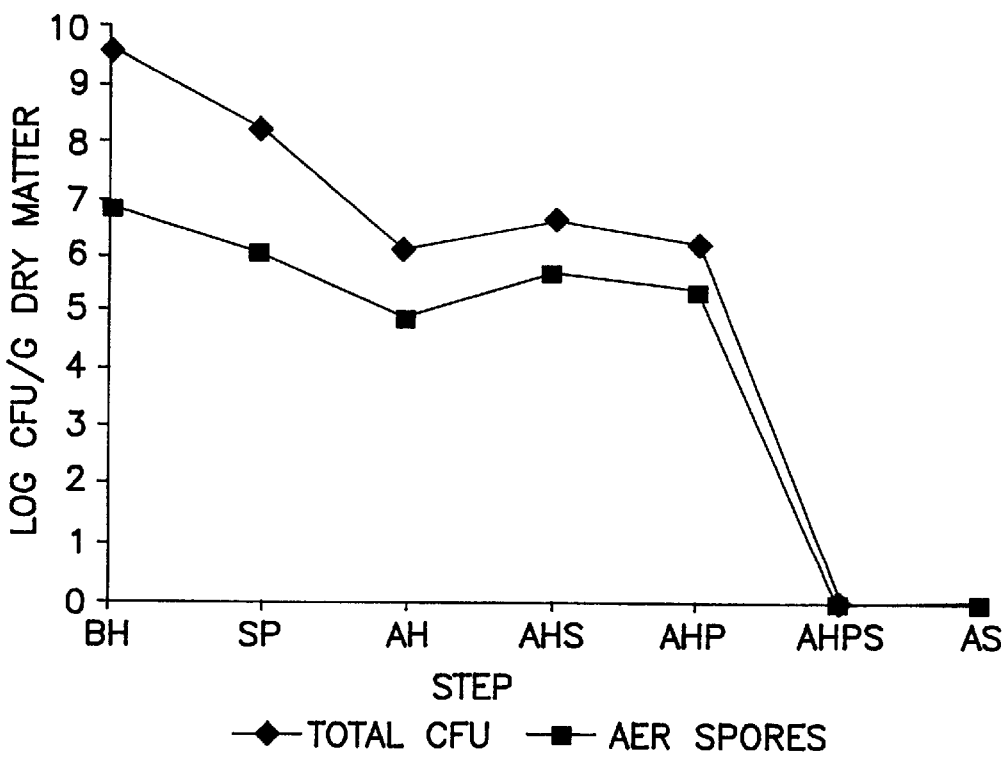
FIG. 4 is a graph of bioburden reduction in OLP pulp of Example 2.

In the graphs depicted in FIGS. 3 and 4, the results from the test runs are presented. The microbial count was determined at different points during the recycling and sanitizing process (see Chart 1 for explanation). The results determined at Tetra Pak Research Stuttgart are shown in FIG. 3, while FIG. 4 shows the results determined at the independent lab, Silliker Laboratories. Only data of the most relevant groups i.e., (aerobic sporeformer, total count and, in FIG. 3 and Table 5, also Enterobacteriaceae) are included in these graphs. As can be seen from Table 5 and Table 6 below, the starting total cfu counts for the untreated OLP pulp material was in the range of about log 9 to log 10. The aerobic spore counts were between about log 6.4 and log 6.8.

The data from Tables 5 and 6 are plotted in the graphs of FIGS. 3 and 4, respectively.

TABLE 5

Reduction of bioburden in pulp from OLP (TPR Stuttgart Results)

| Sample | log total cfu | log aer. spores | log enterobact. |
|---|---|---|---|
| BH | 9.36 | 6.77 | 7.68 |
| SP | 8.59 | 5.53 | 6.38 |
| AH | 5.66 | 4.20 | 2.04 |
| AHS | 5.71 | 4.03 | 2.14 |
| AHP | 2.05 | 0.94 | 0.00 |
| AHPS | 0.00 | 0.00 | 0.00 |
| AS | 0.00 | 0.00 | 0.00 |

TABLE 6

Reduction of bioburden in pulp from OLP (Silliker Laboratories Results)

| Sample | log total cfu | log aer. spores |
|---|---|---|
| BH | 9.58 | 6.75 |
| SP | 8.15 | 6.07 |
| AH | 6.16 | 4.92 |
| AHP | 5.28 | 4.22 |
| AHPS | 0.00 | 0.00 |
| AS | 0.00 | 0.00 |

At the end of module 1 (SP samples), the total count as well as the spore counts are reduced approximately 1 log, which can be attributed to a washing-out effect during module 1. Heating the sample at the end of module 2, at temperatures of about 62–78° C., results in a further 1 log reduction in aerobic spore-formers, and approximately a log 2 to log 3 reduction in the total count. The reduction of Enterobacteriaceae was greater than log 4, due in part to the heat-sensitivity of Gram-negative bacteria. Comparison of the microbial counts for the AH samples with those of the AHS samples demonstrates that storage at 62–78° C., for approximately 10 hours (overnight) after the first heat treatment, did not significantly contribute to a further reduction in the microbial counts. In the TPR Stuttgart results, only the aerobic spore-former counts show a slight reduction, whereas the total count and the Enterobacteriaceae count seem to increase slightly. The observed higher increase in AHS samples evaluated by Silliker Laboratories is probably caused by a longer period between sampling and testing and/or insufficient cooling of samples during storage.

Samples taken at the end of module 3 after the treatment with 1.5% hydrogen peroxide at temperatures of about 82–99° C. (AHP and AHPS samples) shows that such treatment produces a very satisfactory killing effect on all microbial groups (see TPR Stuttgart results). (The results from Silliker Laboratories for the AHP samples should be disregarded because these samples were most likely investigated too long after sampling (about 1 week) and were not adequately stored at the appropriate temperatures.)

AHP samples were treated with $H_2O_2$-inactivating sodium thiosulfate (STS) directly after sampling, whereas AHPS samples were stored without STS inactivation of residual $H_2O_2$. The total counts as well as aerobic spore counts were extremely high in the AHP samples sent to Silliker Laboratories because the microorganisms were able to multiply after the $H_2O_2$ inactivation. In the TPR Stuttgart samples of hydrogen peroxide/heat-treated pulp in module 3, we observed a reduction of almost log 4 in the total count and a reduction of greater than log 3 in aerobic spore count. Samples which were treated with hydrogen peroxide and heat, and stored until testing at ambient temperature at TPR Stuttgart and Silliker Laboratories, displayed microbial counts below the detection limit of $\leq 10$ cfu/g dry matter (reported as log values of 0.00). Thus, these pulp samples had bacterial loads which satisfy IDF recommendations.

Tests showed that all AHP, AHPS and AS samples were free of pathogenic bacteria as determined according to methods described above (anaerobic spores, Enterobacteriaceae, Coagulase-positive Staphylococci, moulds, and yeast).

Moreover, no $H_2O_2$ residues could be found in final pulp samples AHPS and AS, using MERKOQUANT $H_2O_2$ Test sticks (MERCK), which have a detection limit of approximately 0.1 ppm.

5. Discussion of Example 2

The results show that the process of the invention can achieve an extremely good sterilization effect. Specifically, the process achieved a reduction of approximately log 6.8 for Bacillus spores and a reduction of greater than log 9 for total counts. Moreover, no pathogenic bacteria or $H_2O_2$ residues could be found in pulp treated according to the sanitizing process of the invention.

What is claimed is:

1. A process for sanitizing fibers containing microorganisms generated from a post-consumer wastepaper recycle process for food-contact materials, the process comprising:
   (a) providing paper fibers from the wastepaper recycle process;
   (b) adding water to the paper fibers to achieve a slurry;
   (c) de-watering the slurry to obtain a paper fiber stream;
   (d) after forming said fiber stream, passing the fiber stream through a mixing device while heating the fiber stream, and supplying hydrogen peroxide of sufficient amount to the mixing device, thereby sanitizing the fiber stream and wherein the fiber stream is heated to a first temperature effective to open up bacterial spores and then heated to a second temperature effective to kill the spores; and
   (e) using fibers from step (d) to make a paper product having a bacterial load acceptable for a food-contact material.

2. The sanitizing process of claim 1, further comprising:
   (e) adding water to the fiber stream after step (d).

3. The sanitizing process of claim 1, further comprising adding sufficient sodium hydroxide to adjust the pH of the fiber stream to about pH 6–8 in step (c) or (d).

4. The sanitizing process of claim 1, wherein the fiber stream is heated to a temperature in a range from about 80 to about 121° C.

5. The sanitizing process of claim 4, wherein the fiber stream is heated to a temperature in a range from about 90 to about 115° C.

6. The sanitizing process of claim 5, wherein the fiber stream is heated to a temperature in a range from about 110 to about 115° C.

7. The sanitizing process of claim 1, wherein the first temperature is in a range of from about 70 to about 75° C., and the second temperature is in a range from about 80 to about 115° C.

8. The sanitizing process of claim 1, wherein the hydrogen peroxide is in a dilute hydrogen peroxide solution.

9. The sanitizing process of claim 8, wherein the dilute hydrogen peroxide solution is present in a concentration in a range of from about 0.1 to about 5% by volume in the fiber stream.

10. The sanitizing process of claim 9, wherein said dilute hydrogen peroxide solution is present in a concentration in a range of from about 2 to about 4% by volume in the fiber stream.

11. The sanitizing process of claim 1, wherein in step (d), the fiber stream is held in the mixing device for a time in a range from about 0.5 to about 5 minutes.

12. The sanitizing process of claim 11, wherein in step (d), the fiber stream is held in the mixing device for a time in a range from about 2 to about 4 minutes.

13. The sanitizing process of claim 1, wherein step (d) includes supplying steam to the mixing device.

14. The sanitizing process of claim 13, wherein said steam is at a temperature in a range of from about 160 to about 170° C.

15. The sanitizing process of claim 13, wherein said fiber stream is pressurized.

16. The sanitizing process of claim 15, wherein the fiber stream is under pressure in the mixing device.

17. The sanitizing process of claim 1, wherein, in step (c) or step (d), sufficient sodium hydroxide is added to the fiber stream to adjust the pH of the fiber stream to about pH 6–8; wherein, in step (d), the hydrogen peroxide is in a dilute hydrogen peroxide solution, the solution is in a concentration of about 0.1–5% by volume in the fiber stream, steam is supplied to the mixing device, and the fiber stream is held in the mixing device for about 0.5–5 minutes; and further comprising:
   (e) adding water to the fiber stream after step (d).

18. The sanitizing process of claim 17, wherein the fiber stream is heated to a temperature in a range from about 80 to about 121° C. and the steam is pressurized.

19. The sanitizing process of claim 17, further comprising using the fibers from step (e) to make a paper product.

20. The sanitizing process of claim 17, wherein the first temperature is in a range from about 70 to about 75° C. and the second temperature is in a range from about 80 to about 115° C.

21. The sanitizing process of claim 1, wherein the slurry in step (b) has a consistency in a range of from about 0.5 to about 5% paper fibers.

22. The sanitizing process of claim 1, wherein the paper fiber stream of step (c) has a consistency in a range of from about 10 to about 40% fibers.

23. The sanitizing process of claim 1, wherein step (e) includes obtaining a bacterial load no greater than approximately 250 cfu/g.

24. A process for sanitizing fibers containing microorganisms generated from a post-consumer wastepaper recycle process for food-contact materials, the process comprising:

(a) providing paper fibers from the wastepaper recycle process;
(b) adding water to the paper fibers to achieve a slurry;
(c) de-watering the slurry to obtain a paper fiber stream; and
(d) passing the fiber stream through a mixing device while heating the fiber stream, and supplying hydrogen peroxide of sufficient amount to the mixing device thereby sanitizing the fiber stream and wherein the fiber stream is heated to a first temperature effective to open up bacterial spores and then heated to a second temperature effective to kill the spores;
(e) adding water to the fiber stream after step (d); and
(f) using fibers from step (d) or step (e) to make a paper product having a bacterial load acceptable for a food-contact material.

25. The sanitizing process of claim 24, wherein step (f) includes making a paper product having a bacterial load no greater than approximately 250 cfu/g.

* * * * *